US009737486B2

(12) United States Patent
Bright et al.

(10) Patent No.: US 9,737,486 B2
(45) Date of Patent: Aug. 22, 2017

(54) METHOD AND USE OF NANO-SCALE DEVICES FOR REDUCTION OF TISSUE INJURY IN ISCHEMIC AND REPERFUSION INJURY

(71) Applicants: THE JOHNS HOPKINS UNIVERSITY, Baltimore, MD (US); THE BOARD OF TRUSTEES OF THE LELAND STANFORD JUNIOR UNIVERSITY, Stanford, CA (US)

(72) Inventors: Corinne Bright, Los Gatos, CA (US); Rachel Bright, Palo Alto, CA (US); Eric Churchill, Long Beach, CA (US); Kam W. Leong, Durham, NC (US); Daria Mochly-Rosen, Menlo Park, CA (US)

(73) Assignees: THE BOARD OF TRUSTEES OF THE LELAND STANFORD JUNIOR UNIVERSITY, Stanford, CA (US); THE JOHNS HOPKINS UNIVERSITY, Baltimore, MD (US)

( * ) Notice: Subject to any disclaimer, the term of this patent is extended or adjusted under 35 U.S.C. 154(b) by 694 days.

(21) Appl. No.: 14/194,559

(22) Filed: Feb. 28, 2014

(65) Prior Publication Data
US 2014/0178465 A1 Jun. 26, 2014

Related U.S. Application Data

(62) Division of application No. 11/799,573, filed on May 1, 2007, now Pat. No. 8,697,120.

(60) Provisional application No. 60/796,790, filed on May 1, 2006.

(51) Int. Cl.
| *A61K 9/14* | (2006.01) |
| *A61K 9/127* | (2006.01) |
| *A61K 9/51* | (2006.01) |
| *A61K 31/765* | (2006.01) |
| *A61K 31/78* | (2006.01) |
| *A61K 45/06* | (2006.01) |

(52) U.S. Cl.
CPC ............. *A61K 9/14* (2013.01); *A61K 9/5138* (2013.01); *A61K 31/765* (2013.01); *A61K 31/78* (2013.01); *A61K 45/06* (2013.01)

(58) Field of Classification Search
CPC .................................. A61K 9/14; A61K 9/127
See application file for complete search history.

(56) References Cited

U.S. PATENT DOCUMENTS

| 5,103,556 A | 4/1992 | Filip et al. |
| 5,348,016 A | 9/1994 | Unger et al. |
| 5,747,026 A | 5/1998 | Crapo et al. |
| 6,235,308 B1 | 5/2001 | Barenholz |
| 7,008,642 B1* | 3/2006 | Roorda ............... A61K 9/1617 424/423 |
| 2001/0006989 A1* | 7/2001 | Bru-Magniez .......... C08F 22/14 524/265 |
| 2002/0013291 A1 | 1/2002 | Elliot et al. |
| 2002/0110588 A1 | 8/2002 | Hope et al. |
| 2004/0009216 A1 | 1/2004 | Rodrigueza et al. |
| 2006/0067925 A1 | 3/2006 | Labhasetwar et al. |
| 2007/0259032 A1 | 11/2007 | Bright et al. |
| 2010/0249208 A1 | 9/2010 | Hecker et al. |

FOREIGN PATENT DOCUMENTS

| EP | 0461559 B1 | 12/1991 |
| EP | 0520888 A1 | 12/1992 |
| EP | 0512916 B1 | 2/1999 |
| WO | WO 03/086351 A1 | 10/2003 |
| WO | WO 2007/002662 A2 | 1/2007 |

OTHER PUBLICATIONS

Brenton et al., "Physico-chemical characterization, preparation and performance of poly (methylidene malonate 2.1.2) nanoparticles", Biomaterials, vol. 19, No. 1, pp. 271-281 (1998).
International Search Report and Written Opinion for PCT Patent Application No. PCT/US2007/010600, search report dated Jul. 18, 2008.
Van Der Hoeven et al., "Drug-eluting stents: results, promises and problems", Int. J. Cardiol., vol. 99, No. 1, pp. 9-17 (2005).

* cited by examiner

*Primary Examiner* — Gollamudi Kishore
(74) *Attorney, Agent, or Firm* — Jacqueline F. Mahoney; Judy M. Mohr; McDermott Will & Emery LLP

(57) ABSTRACT

A method for protection of tissues subject to ischemic and/or reperfusion damage is provided. The method includes administering to the tissue a composition comprising nanodevices. The nanodevices can take the form of, for example, polymeric nanoparticles or lipidic nanoparticles. The nanodevices also find use in methods for reducing ischemic injury in tissue at risk of such injury, such as heart and brain tissue.

12 Claims, 3 Drawing Sheets

METHOD AND USE OF NANO-SCALE DEVICES FOR REDUCTION OF TISSUE INJURY IN ISCHEMIC AND REPERFUSION INJURY

CROSS REFERENCE TO RELATED APPLICATIONS

The application is a divisional of U.S. application Ser. No. 11/799,573, filed May 1, 2007, now allowed, which claims the benefit of U.S. Provisional Application No. 60/796,790, filed May 1, 2006; each of which is incorporated herein by reference in its entirety.

STATEMENT REGARDING GOVERNMENT INTEREST

This invention was made with Government support under contract HL052141 awarded by the National Institutes of Health. The Government has certain rights in this invention.

TECHNICAL FIELD

The subject matter described herein relates to methods for reducing ischemic and reperfusion-induced tissue injury by delivering nanodevices to achieve a therapeutic benefit under conditions of ischemia/reperfusion.

BACKGROUND

Ischemic and reperfusion injury are major causes of disability and death in the United States. Ischemia is caused by a blockage and cessation of blood flow to a region of tissue, and may occur in multiple tissues, including the heart in diseases such as myocardial infarction and the brain, such as in ischemic stroke. Reperfusion injury may occur following recanalization of an occluded vessel, and reflow of blood into an ischemic area. Reperfusion may cause additional tissue stress, sometimes worsening damage.

Current strategies to protect tissues from the effects of ischemic and reperfusion damage are limited. The primary approach involves the delivery of drugs for prevention, such as anti-platelet agents (e.g. aspirin, abciximab), anti-coagulants (e.g. warfarin, tissue plasminogen activator (tPA)), anti-inflammatory agents (e.g. aspirin), diuretics (e.g. furosemide), vasodilators (e.g. nitroglycerine, ACE inhibitors), and anti-hypertensive medications (e.g. atenolol). Such drugs reduce the causative factors involved in arterial blockage; however, they do not provide protection to a tissue affected by an ischemic event. In addition, not all patients benefit from these treatments, due in part to factors including drug insensitivity, drug toxicities, and other risks (e.g. hemorrhage), and drug interactions.

In addition to drug-based strategies, approaches have been developed to diminish the injury associated with an acute ischemic event. Such techniques focus on restoring blood flow by use of angioplasty, arterial stenting, coronary bypass, and treatment with thrombolytic drugs (e.g. tPA). These treatments may improve patient prognosis, however, tissue damage can occur from the procedure including the acute risk of vessel rupture and ischemic damage, and delayed risks include restenosis, or reocclusion of the occluded vessel leading to additional ischemic events. For example, following arterial stenting procedures, restenosis occurs in 10-40% of cases (van der Hoeven, B. L. et al., *Int J. Cardiol.*, 99(1):9 2005).

There a need for a treatment method for reducing tissue damage in an ischemic and reperfusion events. In addition, there exists a need for nanodevices for the treatment of patients, including patients in which current pharmaceutical solutions are unacceptable.

BRIEF SUMMARY

The following aspects and embodiments thereof described and illustrated below are meant to be exemplary and illustrative, not limiting in scope.

In one aspect, a method for reducing ischemic reperfusion injury is provided by delivering intravascularly a composition comprised nanodevices. Delivery of such nanodevices is beneficial in methods for tissue protection and for reducing tissue damage subsequent to an ischemic event.

In another aspect, methods for protecting cardiac tissue in a mammalian heart prone to, characterized by, or otherwise experiencing, ischemic injury due to a disease or condition, such as myocardial infarction, are provided. In one embodiment, a method for decreasing tissue damage in such a mammalian heart includes administering to a patient in need thereof an effective concentration of a nanodevice. Nanodevices include nanoparticles, nanorods, nanospheres, microspheres, liposomes, micelles, microbubbles, or nanobubbles. In certain embodiments, the agent is a polymer nanoparticle, and is further described as poly(methylidene malonate 2.1.2) (PMM 2.1.2). More generally, and in another embodiment, the nanodevice is comprised of a polymer, including biodegradable polymers, such as poly(lactic-co-glycolic acid). Other polymers that may advantageously be used in the methods are further described below The methods may advantageously be used to decrease ischemic and/or reperfusion injury in conditions characterized by ischemic damage. The methods may also be utilized to decrease ischemic damage in multiple other tissues in vivo (such as the brain, kidney, or liver) for any other purpose where tissue protection against ischemic damage is desired, including but not limited to, during organ and tissue harvest and transplantation and during surgeries in which blood supply to the organ is temporarily interrupted.

In another aspect, methods for delivery of agents which confer tissue protection against a timed (or scheduled) ischemic event (e.g., surgery) or untimed ischemic event (e.g., myocardial infarction or stroke) are provided. In one embodiment, a patient is provided with an effective concentration of a nanodevice within a clinically-relevant timeframe prior to the surgery. In one embodiment, this time frame is less than 48 hours, preferably less than 24 hours, more preferably less than 12 hours prior to surgery, still more preferably within about 6 hours prior to surgery. Alternatively, the nanodevices are delivered chronically (i.e., for an indefinite period of time) to reduce damage from an untimed ischemic event, for example to a person at risk of myocardial infarction or stroke. Chronic delivery may be every month, week, day, or hour.

In another aspect, methods for intra-vascular delivery of nanodevices to confer a therapeutic benefit are provided. In one embodiment, nanodevices are delivered via a directly supplying artery or vein to the target tissue prior to an ischemic event. In various embodiments, the nanodevices are injected intravascularly, e.g., at peripheral sites for systemic delivery to achieve a therapeutic benefit.

In other aspects, methods for decreasing tissue damage in a mammalian tissue characterized by, or otherwise experiencing, an ischemic or reperfusion event due to a disease or condition, such as myocardial infarction, are provided.

In still other aspects, methods for reducing tissue damage in a mammalian tissue prone to, characterized by, or otherwise experiencing, ischemic injury due to a disease or condition, such as myocardial infarction, in patients that are unresponsive, desensitized, or otherwise unable to benefit from available drug agents, are provided. Such patients include those receiving drugs or not receiving drugs.

In related aspects, the use of a nanodevice for the preparation of a medicament for administration to a subject for protecting tissue from ischemic injury is provided. In some embodiments, the nanodevice is a plurality of nanodevices.

In some embodiments, the nanodevice is selected from the group consisting of nanoparticles, nanorods, nanospheres, liposomes, micelles, and nanobubbles.

In some embodiments, the nanodevice is a polymeric nanodevice. In particular embodiments, the polymer is a biodegradable or nonbiodegradable polymer.

In some embodiments, the polymer is poly(methylidene malonate 2.1.2) (PMM 2.1.2).

In some embodiments, the subject is at risk of myocardial infarction. In some embodiments, the subject is at risk of ischemic damage due to myocardial infarction or stroke. In some embodiments, the administering to a subject is prior to surgery.

In another aspect, the use of a nanodevice for the preparation of a medicament for administration to a subject intravascularly for reducing ischemic reperfusion injury to a tissue is provided.

In some embodiments, the medicament is administered during organ or tissue harvest. In some embodiments, the medicament is administered during organ or tissue transplantation. In some embodiments, the medicament is administered during surgery.

In some embodiments, the nanodevices are polymeric nanodevices. In some embodiments, the nanodevices are lipidic nanodevices.

In another aspect, the use of a nanodevice for the preparation of a medicament for administration to a subject intravascularly for conferring protection to a tissue at risk of ischemic injury, wherein the nanodevice is a polymer or lipidic nanodevice, is provided.

In some embodiments, the medicament is administered prior to a scheduled ischemic event. In some embodiments, the scheduled ischemic event is surgery. In particular embodiments, the medicament is administered at least about 12 hours prior to surgery.

In some embodiments, the medicament is administered chronically prior to an unscheduled ischemic event. In particular embodiments, the medicament is administered at least about monthly.

In some embodiments, the lipidic nanodevices are administered in the form of liposomes or micelles.

In all embodiments, the medicament may further comprise an additional therapeutic agent.

In addition to the exemplary aspects and embodiments described above, further aspects and embodiments will become apparent by reference to the drawings and by study of the following descriptions.

DETAILED DESCRIPTION

Figure 1:
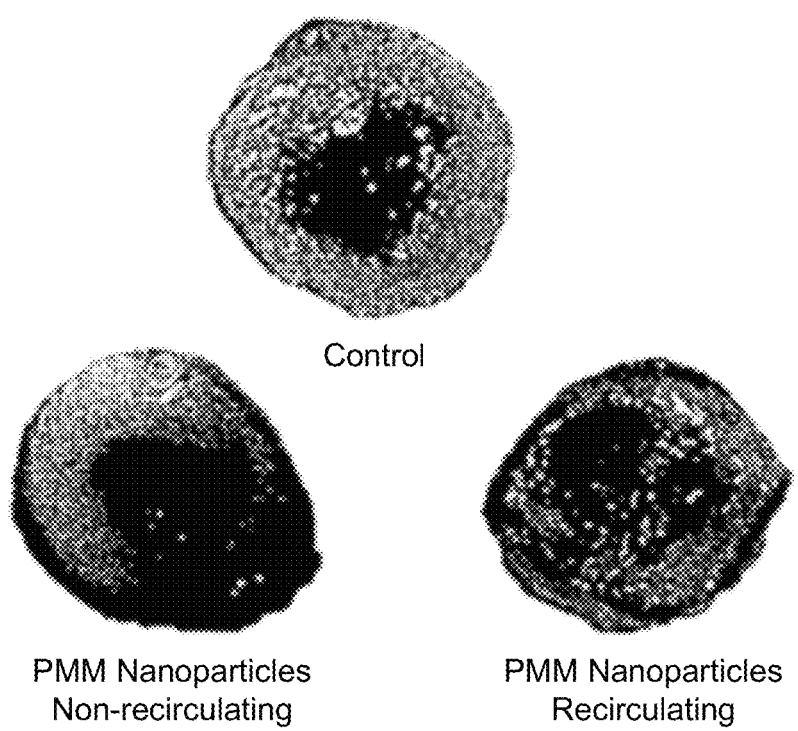
FIG. 1 shows images of heart slices obtained from animals exposed to ischemic reperfusion injury with mock-treatment (control) or ischemic reperfusion injury with prior intravascular infusion of nanoparticles (PMM nanoparticles), with or without recirculation of perfusate buffer (i.e., recirculating, non-recirculating, respectively).

In one aspect, methods of decreasing tissue damage in a vertebrate tissue prone to, characterized by, or otherwise experiencing, ischemic injury due to a disease or condition are provided. As used herein, "ischemia" refers to an event that causes a cell, tissue, or organ to receive an inadequate supply of oxygen. It has been discovered that intravascular delivery of nanodevices to an organ affected by ischemia and/or reperfusion reduces tissue damage under conditions of ischemia and reperfusion. In addition, it has been discovered that delivery of nanodevices prior to an ischemic event significantly reduces damage caused by a subsequent ischemia.

I. Nanodevices

In one embodiment, the present methods include administering to a patient in need thereof a therapeutically effective dose of nanodevices. As used herein, a "nanodevice" refers to a device that is of a size between 1-10,000 nm, more preferably between 10-5,000 nm, and still more preferably between 10-1,000 nm. The nanodevice may be of virtually any geometry, including but not limited to nanoparticles, nanospheres, nanorods, and nanobubbles. An exemplary nanoparticle is a polymeric nanoparticle. Another exemplary nanoparticle is a lipidic nanoparticle, such as a liposome or a micelle. These devices may have modifications as described below to enhance the therapeutic effect, improve delivery, tissue targeting, biocompatibility, stability, pharmacokinetics, toxicity, or other benefits. The term nanoparticle may be used to refer generally to the nanodevice but should not be construed as limiting.

In one embodiment, polymers may be used to form nanoparticles or microparticles. This polymer may a natural or synthetic polymer, hydrophilic or hydrophobic, biodegradeable or non-biodegradable. Exemplary biodegradable polymers include but are not limited to polyesters including polylactic acid) (PLA), poly (lactic-co-glycolic acid) (PLGA), poly(glycolic acid) (PGA), poly-e-caprolactone (PCL), or polyanhydrides (e.g., bis(p-carboxyphonoxy) propane and sebacic acid). Natural polymers include but are not limited to gelatin, collagen, keratin, chitosan, alginate, and other natural polymers known in the art. Non-biodegradeable polymers include but are not limited to methylcellulose, polyacrylamide, poly-2-hydroxyethyl methacrylate, polyhydroxyethyl methacrylate (pHEMA), polymethylmethacrylate (PMMA), polyvinyl alcohol (PVA), and polyethylene glycol (PEG). Homopolymers may be combined to form di and tri-block copolymers, and/or other combinations thereof. A range of molecular weights from, for example, 1 kDa to 1 megaDa, may be used. In general, a variety of polymers with a range of positive, negative, or neutral charges can be used, as in, for example, co-polymers with various ratios of polymer components. Polymers can be selected on the basis of several parameters including size, surface characteristics (including charge), biocompatibility, minimal cytotoxicity and immunogenicity, or other adverse side effects.

In another embodiment, lipids are used to form micellar or liposomal nanoparticles. Formation of micelles and liposomes from, for example, vesicle-forming lipids, is known in the art. Vesicle-forming lipids refer to lipids that spontaneously form lipid bilayers above their gel-to-liquid crystalline phase transition temperature range. Such lipids typically have certain features that permit spontaneous bilayer formation, such as close to identical cross-section areas of their hydrophobic and hydrophilic portions permitting packing into lamellar phases. Lipids capable of stable incorporation into lipid bilayers, such as cholesterol and its various analogs, can be incorporated into the lipid bilayer during bilayer formation. The vesicle-forming lipids are preferably lipids having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two-hydrocarbon chains are typically between about 14-22 carbon atoms in length, and either saturated or having varying degrees of unsaturation. The above-described lipids and phospholipids whose acyl chains have varying degrees of saturation can be obtained commercially or prepared according to published methods. Other suitable lipids include phospholipids, sphingolipids, glycolipids, and sterols, such as cholesterol.

Polymeric and lipidic nanodevices can additionally include a coating of a hydrophilic polymer. For example, the nanodevices can include a polymer-polyethylene glycol or a lipid-polyethylene glycol conjugate, to provide an external surface coating of polymer chains. The polymer polyethylene glycol is exemplary, and other polymers are suitable and are contemplated. Preparation of a vesicle-forming lipid derivatized with a hydrophilic polymer to form a lipopolymer is described, for example in U.S. Pat. No. 5,013,556. It will also be appreciated that the polymer or lipidic nanodevice can be formed from multiple layers of the same or different material.

A variety of nanodevice sizes may be used based on factors including the concentration, route of delivery, target tissue and disease application. Sizes from about 1 to 10,000 nm, more preferably 1 to 1,000 nm, and still more preferably 100 to 600 nm, are contemplated.

A wide variety of modifications to the nanodevices may be made and are known in the art. Such modifications may include coating the nanodevice with surfactants (e.g. PEG-lyation), stabilizers (e.g. dextran, MW 50,000-70,000), or agents that enhance delivery or targeting to tissues, such as targeting moieties, including but not limited to antibodies and antibody fragments with specific binding to a cell surface receptor.

The nanodevice may also be coated or impregnated with a therapeutic agent; however, it is appreciated that the nanodevice alone (e.g., with no coated or impregnated therapeutic agent) provide a therapeutic effect. In some embodiments, addition of a therapeutic agent to the nanodevice, e.g., to provide an additional, different, or synergistic response, is contemplated. As used herein, a "therapeutic agent," or additional therapeutic agent," refers to any molecule, e.g., protein, oligopeptide, small organic molecule, polysaccharide, polynucleotide, etc., which can be attached to a nanodevice for subsequent release. Such therapeutic agents include anti-platelet agents (e.g., aspirin, abciximab), anti-coagulants (e.g., warfarin, tPA), anti-inflammatory agents (e.g., aspirin), diuretics (e.g., furosemide), vasodilators (e.g. nitroglycerine, ACE inhibitors) and anti-hypertensive agents (e.g., atenolol). In one embodiment, a single drug is loaded or impregnated into the nanodevice. In another embodiment, multiple drugs are loaded or impregnated into the device, e.g., for co-delivery to a patient. Such therapeutic agents may be used to enhance or provide additional therapeutic benefits.

The nanodevice may also contain or be coated with non-therapeutic agents to enhance the delivery of drugs, protect the drugs from degradation or stabilize the drug during processing, storage, or patient use, or protect the polymer material from adverse effects during processing, storage or patient use. In addition, the nanodevice may contain agents that reduce toxicity or adverse side effects of the delivered drug, or enhance the activity of the drug or non-therapeutic agent described above in the body. In addition, the nanodevice may contain agents that enhance targeting of the drug or agent to specific regions of the body, including different cell types, tissues, or organs.

II. Administration of Nanodevices

According to the present methods, a therapeutically effective amount of the nanodevice is delivered to a patient. As used herein, "a therapeutically effective amount" of the nanodevice is the quantity of the nanodevice required to achieve a desired clinical outcome, such as a decrease in infarct size in a mammalian heart due to an ischemic or other cell damaging event. This amount will vary depending on the time of administration (e.g., prior to an ischemic event, at the onset of the event or thereafter), the route of administration, the duration of treatment, the specific nanodevice used, and the characteristics (including the health) of the patient, as known in the art. The skilled artisan will be able to determine the optimum dosage.

Generally, the concentration or dosage of a nanodevice for use according to the present methods is about 100 to 10,000 million particles/mL, but is preferably about 10 to 100,000 million particles/mL. Alternatively, approximately 10 µL to 10 mL, and preferably 100 µL to 1 mL, of an 0.0001% to 2.5% aqueous nanodevice suspension, and preferably a 0.00025% to a 0.0025% aqueous suspension, is delivered endovascularly.

The nanodevices are typically administered parenterally, with intravenous administration being preferred. It will be appreciated that the nanodevices can include any necessary or desirable pharmaceutical excipients to facilitate delivery. Exemplary excipients include, but are not limited to water, saline, buffers, oils, or other liquids. The carrier may be selected for intravenous or intraarterial administration, and may include a sterile aqueous or non-aqueous solution that may include preservatives, bacteriostats, buffers, and/or antioxidants known to the art.

Administration of the nanodevices can be to any tissue or organ in the body for protection from ischemic damage or reduction of ischemic damage. Delivery of nanodevices to protect or reduce damage in the heart, liver, kidney, brain, etc. are contemplated. One skilled in the art will recognize that the described nanoparticles can be used to prepare a medicament for administration to a mammalian patient for reducing cellular damage due to ischemia.

III. Proposed Mechanism

The mechanism of action is not critical to the present methods. However, a proposed mechanisms of action includes, but is not limited to, causing minor damage to cells or tissues associated with a target organ, or peripheral cells or tissues, thereby causing the release of endogenous cytoprotective agents, which confer tissue protection. This method of tissue protection is illustrated in the example below, in particular with respect to the use of PMM nanoparticles in an animal model for cardiac ischemic and reperfusion injury.

EXAMPLES

Reference will now be made to specific examples illustrating aspects and embodiments described above. The examples are provided to illustrate preferred embodiments and should not be construed as limiting the scope of the subject matter.

Example 1. Nanodevices for Reducing Ischemic Injury

The present example shows that reduced tissue damage was achieved in a rat heart subject to ex vivo ischemia and reperfusion injury by treating the heart with nanoparticles.

A. Materials

Male Sprague-Dawley rats (280-380 g; n=4-5 per group) were used for ex vivo cardiac ischemia and reperfusion. PMM nanoparticles were synthesized via polymerization of poly(methylidene malonate 2.1.2 monomer as described previously (Breton, P. et al., *Biomaterials*, 19(1-3):271 (1998)). Polymer was delivered at $1\times10^6$ particles/mL to the heart.

B. Methods

To mimic acute myocardial infarction, an ex vivo Langendorff cardiac ischemia/reperfusion model was used. Working hearts were extracted from deeply anesthetized animals and rapidly cannulized. Oxygenated, warmed Krebs buffer was perfused in a retrograde fashion through the hearts via the aorta to maintain tissue viability. To mimic ischemia, perfusion of the oxygenated buffer was stopped for a period of 40 minutes. Reperfusion was performed by recommencing cardiac perfusion of buffer for a period of 60 minutes. During the reperfusion period, perfusate from the heart was collected to measure creatine phosphokinase (CPK) levels. CPK is a molecule released from necrotic cardiomyocytes, which is used to monitor the extent of cardiac infarction. Following reperfusion, hearts were sliced and stained with triphenyl tetrazolium chloride (TTC), a mitochondrial stain that delineates live/dead tissue. Infarct size was quantitated by measuring the area of infarction with respect to the total heart surface.

Hearts underwent treatment with either sham buffer (control) or a buffer containing PMM nanoparticles, for 10 minutes prior to ischemia. This buffer was either re-circulated through the heart in a closed-loop system or, in different sets of experiments, received fresh buffer in an open loop system. CPK levels were monitored from heart perfusate during the period of reperfusion for additional quantitation of cell damage.

C. Results

Figure 2A:
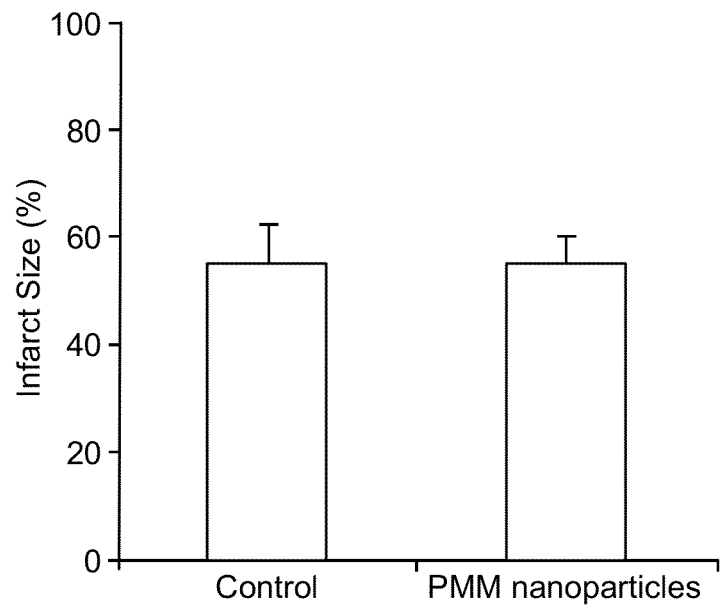
FIGS. 2A and 2B are graphs showing the average infarct sizes in hearts subject to ischemic-reperfusion injury with mock-treatment (control), or with prior intravascular infusion of nanoparticles, with without recirculation of the perfusate buffer (A), or with recirculation of the perfusate buffer (B). (*$p<0.05$—statistical significance between groups assessed by students t-test).
Figure 2B:
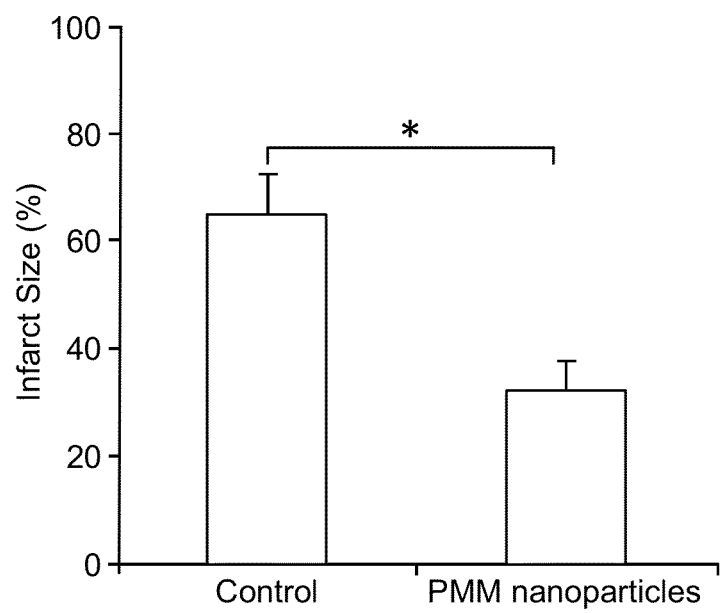
Figure 3:
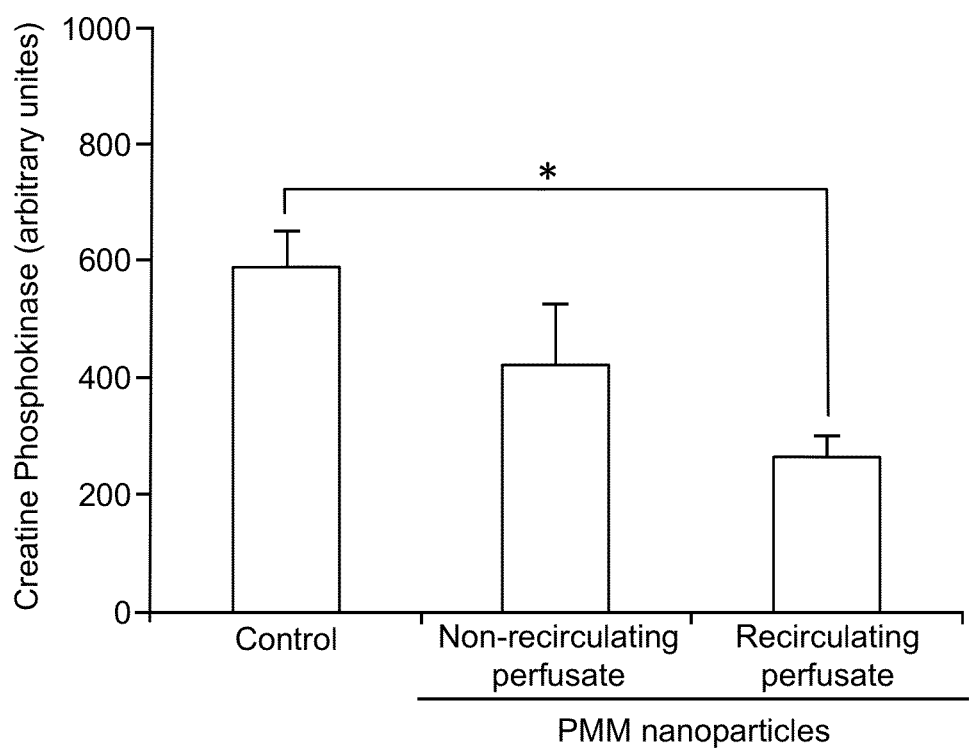
FIG. 3 is a graph showing the average creatine phosphokinase levels in hearts subject to ischemic-reperfusion injury with mock-treatment, or with prior intravascular infusion of nanoparticles, with our without recirculation of the perfusate buffer (*$p<0.05$—statistical significance between groups assessed by students t-test).

Results are shown in FIGS. 1, 2, and 3. In sham-buffer-treated animals, a large area of cardiac infarction developed (FIGS. 1, 2), which corresponded to high CPK levels (FIG. 3). When PMM nanoparticles were perfused through the heart, using recirculation of perfusate back through the heart, a substantial reduction in infarct size was achieved (FIGS. 1, 2), corresponding to a decrease in CPK levels (FIG. 3). Thus, delivery of nanodevices to the animals conferred protection from tissue damage due to ischemia. In contrast, when nanoparticles were not re-circulated through the heart in the perfusate buffer, no significant protection was afforded (FIGS. 1, 2, 3).

Without being bound by theory, the results suggest that one or more endogenous releasable factors (e.g., adenosine) is stimulated upon delivery of nanodevices, and such endogenous releasable factors mediate a protective effect. The endogenous factor(s) could be released due to the interaction of the nanoparticle on the target tissue, and/or may further be due to interaction of the nanoparticles with the vessel wall, causing stress, such as shear-stress, and cellular responses, such as release of endogenous vasodilating or cytoprotective agents.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

Example 2. Identification of Optimal Surface Characteristics of Nanodevices

Nanodevices having surface characteristic optimal for delivering and releasing therapeutic agents (i.e., drugs) are determined by testing a series of nanodevices, e.g., in the animal model described in Example 1.

In one experiment, the following nanodevices are tested.

| Nanodevices with differing surface characteristics will be evaluated for cardioprotective effects | | | |
|---|---|---|---|
| Surface characteristics | Size | Name | Fluorophore ($\lambda$) |
| Negative charge | 0.5 μm | PMM 2.1.2 | 580/605 |
| Positive charge | 0.2 μm | FS amine | 580/605 |
| Positive charge | 1.0 μm | FS amine | 505/515 |
| Carboxylate modified | 0.2 μm | FS carboxylate | 580/605 |
| Carboxylate modified | 0.5 μm | FS carboxylate | 580/605 |
| Carboxylate modified | 1.0 μm | FS carboxylate | 580/605 |

Each nanodevice is tested as described, e.g., in Example 1, with results being determined by measuring the levels of cardiac enzymes released in the buffer effluent (a measure of oncosis) as well as by staining with triphenyl tetrazolium chloride (TTC) to measure tissue necrosis.

Upon identifying the optimal nanodevice surface for eliciting protection, experiments are performed to determine if the particular surface characteristics are required for endothelial interactions. Tissue collected from the above study is cut into 5-micron transverse sections via a cryostat, and then mounted and fixed on a glass slide. The sections are co-stained for nuclei (DAPI) and an endothelial marker (CD31). Fluorescent images are obtained using a laser scanning confocal microscope (Pascal, Zeiss) with the appropriate excitation/emissions wavelength for the fluorophore, as provided in the above Table.

These experiments determine the optimum surface for eliciting protection and whether such surfaces facilitate interaction between the nanodevices and the epithelium of a transplant organ.

Example 3. Measuring Adenosine Concentration in Cardiac Tissue

Preliminary studies suggest that nanodevices protect allografts via an adenosine receptor-dependent mechanism.

However, the short half-life of adenosine (<1 second in the blood) makes studying this mechanism problematic. An inhibitor of adenosine deaminase (the enzyme responsible for degradation of adenosine and used for snap freezing) is used to facilitate study the mechanism. Briefly, hearts are perfused with cardioprotective nanoparticles for 2 minutes. A cold 15 G needle is used to collect biopsy samples every 30 seconds. The biopsy samples are snap frozen in tubes containing extraction buffer (0.4 M perchloric acid) and 280 µM deaminase inhibitor (e.g., erythro-9(2-hydroxy-3-nonyl) adenine; EHNA. Following two freeze/thaw cycles, shaking, and centrifugation, the samples are loaded onto a reverse-phase HPLC column to separate adenosine from other nucleotide catabolites. Samples are normalized to an adenosine standard and the relative amount of adenosine is recorded.

The difference in adenosine levels between organs treated with a nanodevice and untreated organs indicates the effect of the nanodevice treatment. For example, elevated levels of adenosine following nanodevice treatment suggest that the mechanism of action of the nanodevices involves increasing adenosine levels.

Example 4. Determining the Activity of 5' Nucleotidase

Adenosine is generated from the 5' nucleotidase-mediated catabolism of AMP. To determine if the activity of this enzyme is altered by treatment with nanodevices, treated and untreated organs (e.g., hearts) are perfused for 2 minutes with nanoparticles. Needle biopsy samples are then collected, snap-frozen, and ground using a mortar and pestle cooled with liquid nitrogen. The production of adenosine is monitored spectrophotometrically at 340 nm upon addition of AMP to biopsy material. Specificity of adenine production may be determined by addition of the 5'nucleotidase inhibitor alpha, beta-methylene adenosine 5'-diphosphate (AOPCP), which should prevent the production of adenosine by the subject pathway. Samples may normalized to an adenosine standard.

The invention claimed is:

1. A method for reducing ischemic reperfusion injury to a tissue, comprising administering intravascularly to the tissue a composition comprising a nanodevice having a diameter of about 10-1000 nm, wherein said nanodevice is selected from the group consisting of nanoparticles, nanorods, nanospheres, and nanobubbles in the absence of a therapeutic agent.

2. The method of claim 1, wherein said administering comprises administering during organ or tissue harvest.

3. The method of claim 1, wherein said administering comprises administering during organ or tissue transplantation.

4. The method of claim 1, wherein said administering comprises administering during surgery.

5. The method of claim 1, wherein said administering comprises administering polymeric nanodevices.

6. A method for conferring protection to a tissue at risk of an ischemic reperfusion injury, comprising administering intravascularly to the tissue a composition comprised of polymer or lipidic nanodevices in the absence of a therapeutic agent, each nanodevice having a diameter of between about 10-1000 nm, wherein said nanodevice is selected from the group consisting of nanoparticles, nanorods, nanospheres, and nanobubbles.

7. The method of claim 6, wherein said administering comprising administering prior to a scheduled ischemic event.

8. The method of claim 7, wherein said scheduled ischemic event is surgery.

9. The method of claim 8, wherein said administering is at least about 12 hours prior to surgery.

10. The method of claim 6, wherein said administering comprising administering chronically prior to an unscheduled ischemic reperfusion event.

11. The method of claim 10, wherein said administering is at least about monthly.

12. The method of claim 1, wherein said nanodevice comprises a plurality of nanoparticles, nanorods, nanospheres, or nanobubbles, each having a diameter of between about 10-1000 nm.

* * * * *